United States Patent [19]
Kawashima et al.

[11] Patent Number: 5,876,668
[45] Date of Patent: Mar. 2, 1999

[54] AUTOMATIC BIOCHEMICAL ANALYZER

[75] Inventors: Kiyoshi Kawashima; Shin Saito; Akio Kimura, all of Tokyo; Minoru Inatsugu, Saitama, all of Japan

[73] Assignee: JOEL Ltd., Tokyo, Japan

[21] Appl. No.: 902,815

[22] Filed: Jul. 30, 1997

[51] Int. Cl.⁶ .................................................. G01N 35/10
[52] U.S. Cl. ............................. 422/64; 422/63; 422/67; 436/43; 436/47; 436/49; 436/50; 436/179; 436/180
[58] Field of Search ................................... 422/63, 64, 67, 422/104; 436/43, 47, 48, 49, 50, 174, 179, 180

[56] References Cited

U.S. PATENT DOCUMENTS

| | | | |
|---|---|---|---|
| 4,522,493 | 6/1985 | Tamagawa et al. | 356/36 |
| 4,640,821 | 2/1987 | Mody et al. | 422/81 |
| 4,746,491 | 5/1988 | Ohlin | 422/103 |
| 4,826,775 | 5/1989 | Burns et al. | 436/179 |
| 4,997,627 | 3/1991 | Bergkuist et al. | 422/81 |
| 5,037,612 | 8/1991 | Takahashi et al. | 422/64 |
| 5,094,961 | 3/1992 | Del valle et al. | 436/180 |
| 5,212,094 | 5/1993 | Ogawa | 436/47 |
| 5,320,966 | 6/1994 | Mitsumaki et al. | 436/47 |
| 5,434,083 | 7/1995 | Mitsumaki et al. | 436/48 |
| 5,587,129 | 12/1996 | Kurosaki et al. | 422/64 |
| 5,679,575 | 10/1997 | Kubota et al. | 436/49 |
| 5,731,211 | 3/1998 | Ohlin | 436/179 |
| 5,741,461 | 4/1998 | Takahashi et al. | 422/67 |

FOREIGN PATENT DOCUMENTS

5-2024  1/1993  Japan.

Primary Examiner—Long V. Le
Attorney, Agent, or Firm—Webb Ziesenheim Bruening Logsdon Orkin & Hanson, P.C.

[57] ABSTRACT

There is disclosed a small-sized automatic biochemical analyzer requiring reduced amounts of reagents. An original sample is transferred to diluting containers on a diluting turntable. The diluted sample is transferred to reaction containers on a reaction turntable and analyzed. The original sample is once diluted. The aliquots of sample are taken from the diluted sample. Thus, a limitation imposed by the minimum volume of liquid that the instrument can meter out can be overcome. Let N be the total number of the diluting containers on the diluting turntable. The turntable is rotated in M pitches at a time. M and N do not have any common factor.

9 Claims, 4 Drawing Sheets

AUTOMATIC BIOCHEMICAL ANALYZER

FIELD OF THE INVENTION

The present invention relates to an automatic biochemical analyzer for collecting photometric data from plural reaction containers successively while rotating the containers into which aliquots of samples and reagents are pipetted and, more particularly, to an automatic biochemical analyzer having metering and diluting functions.

BACKGROUND OF THE INVENTION

Automatic chemical analyzers capable of analyzing a biochemical sample, such as blood or urine, in terms of plural items have been already proposed. For example, an automatic chemical analyzer described in Japanese Patent Laid-Open No. 2024/1993 comprises a sample disk holding a plurality of sample containers, a reaction disk holding a plurality of reaction containers, and a plurality of reagent disks holding a plurality of reagent containers. In this instrument, aliquots of sample in the sample containers set on the sample disk are drawn in by a pipetting mechanism and dispensed into the reaction containers on the reaction disks. Another pipetting mechanism draws in reagents from plural reagent disks and feeds the reagents into reaction containers. Thus, the sample is chemically analyzed in terms of various items in each reaction container.

The sample and the reagent are held in their respective containers. Predetermined amounts of these sample and reagent are taken from the containers by pipettes and dispensed into the reaction containers. The volume of liquid that the instrument can meter out has a limitation. For example, the liquid mass around the tip of a pipette breaks at a location that is not fixed. Therefore, in the prior art technique, the minimum amount of liquid that can be metered with sufficient reproducibility is about 3 $\mu$l.

Generally, in a chemical analyzer, the amounts of a sample and a reagent put into a reaction container are set to a ratio of 100:1, taking account of the dynamic range of the induced chemical reaction. Since reagents are expensive, it is desired to minimize the amounts of reagents used. Accordingly, it may be considered to reduce the amount of sample subjected to a reaction. However, because of the limitation described above, it is impossible to reduce the amount of sample below about 3 $\mu$l at present.

SUMMARY OF THE INVENTION

The present invention has been made to solve the foregoing problems.

It is an object of the present invention to provide an automatic biochemical analyzer equipped with a sample-diluting mechanism to reduce the amount of sample required while still utilizing aliquots of sample at the minimum volume level that can be metered, whereby the amount of reagent used can be reduced.

It is another object of the invention to provide an automatic biochemical analyzer permitting accurate dilution.

It is a further object of the invention to provide an automatic chemical analyzer capable of accommodating itself to various items of analysis without the need to use larger diluting containers.

It is a yet other object of the invention to provide an automatic biochemical analyzer that can be designed with increased degrees of freedom without the need to increase the size of the turntable of the diluting mechanism.

It is a still other object of the invention to provide an automatic biochemical analyzer capable of analyzing a sample in terms of plural items only with a single diluting container.

It is an additional object of the invention to provide an automatic biochemical analyzer capable of easily repeating analysis by the use of a diluting mechanism, irrespective of the original material used.

It is a still further object of the invention to provide an automatic biochemical analyzer in which an analytical unit can achieve its potential even if a diluting system having throughput lower than that of the analytical unit is used.

These objects are achieved in accordance with the teachings of the invention by an automatic biochemical analyzer comprising: a sample turntable having sample containers arranged thereon, the sample containers holding an original sample; a diluting turntable having diluting containers arranged thereon; a diluting pipette for drawing in the original sample from the sample containers and discharging the sample into the diluting containers together with a diluent; a reaction container turntable having reaction containers arranged thereon; and a sampling pipette for drawing in the diluted sample from the diluting containers and dispensing the diluted sample into the reaction containers.

In the present invention, the sample is once diluted before reaction. Consequently, it is possible to overcome the limitation imposed on the minimum metered volume of sample as described above. In consequence, the amounts of reagents used can be reduced.

In one feature of the invention, the diluting turntable is rotated in M pitches at a time. Let N be the total number of the diluting containers on the diluting turntable. M and N do not have any common factor. Therefore, the components of the diluting mechanism can be arranged with increased degrees of freedom. As a result, the instrument can be miniaturized.

Other objects and features of the invention will appear in the course of the description thereof, which follows.

DETAILED DESCRIPTION OF THE INVENTION

Figure 1:
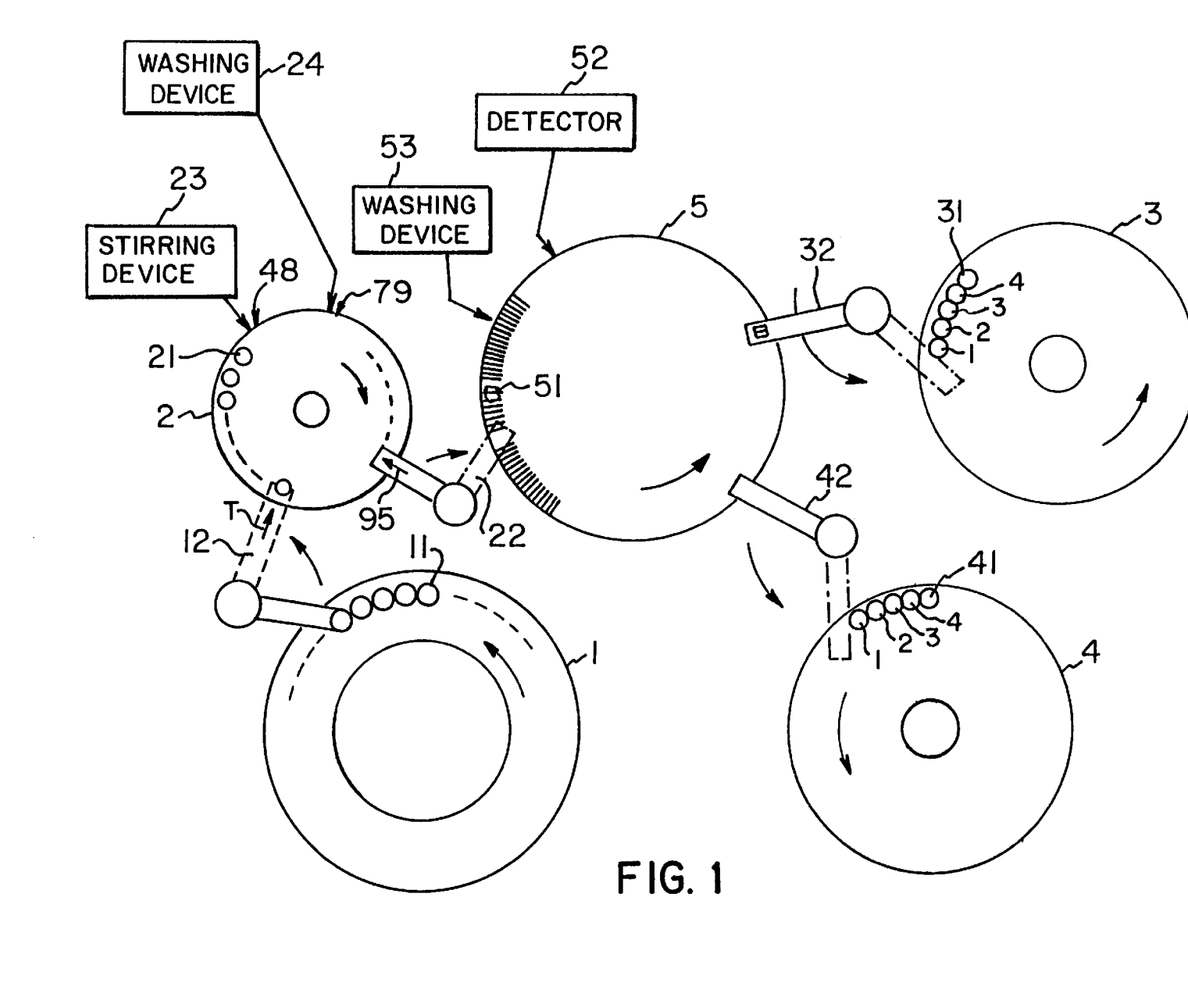
FIG. 1 is a schematic representation of an automatic biochemical analyzer in accordance with the present invention.

The whole structure of an automatic biochemical analyzer in accordance with the present invention is shown in FIG. 1. This analyzer is comprised of a sample turntable 1, a diluting turntable 2, a first reagent turntable 3, a second reagent turntable 4, and a reaction turntable 5 for holding plural reaction containers 51. A sample withdrawn from a living organism is held in plural sample containers 11, which in turn are set on the sample turntable 1. The diluting turntable 2 holds plural diluting containers. Each of the reagent turntables 3 and 4 holds plural reagent containers. A diluting pipette 12 for diluting the original sample and injecting it into the diluting containers on the diluting turntable is disposed between the sample turntable 1 and the diluting turntable 2. A sampling pipette 22 for transferring the diluted sample from the diluting containers to the reaction containers is mounted between the diluting turntable 2 and the reaction turntable 5. A reagent pipette 32 for pipetting a reagent into reaction containers is arranged between the first reagent turntable 3 and the reaction turntable 5. Similarly, another reagent pipette 42 for pipetting another reagent into reaction containers is located between the second reagent turntable 4 and the reaction turntable 5.

The sample containers 11 are arranged circumferentially in two rows on the sample turntable 1. For example, each circumferential row is comprised of 42 sample containers 11. In each row, the sample containers 11 are regularly spaced from each other by a substantially uniform pitch of 360°/42. The turntable 1 is advanced incrementally, one pitch at a time.

The diluting containers are arranged circumferentially in one row on the diluting turntable 2. For example, the number of the diluting containers is 120. These diluting containers are equally spaced from each other by a uniform pitch of 3° (=360°/120). The diluting turntable 2 is advanced incrementally, for example, 47 pitches at a time. The reaction containers 51 are arranged circumferentially in one row on the reaction turntable 5. For instance, the number of the reaction containers 51 is 221.

When one of the sample containers 11 reaches an aspirating position of the sample turntable 1, the diluting pipette 12 draws in a given amount of the original sample from this sample container 11. The aspirated sample is discharged into the diluting container 21 in an injecting position of the diluting turntable 2, along with a diluent supplied from the diluting pipette itself. As a result, the original sample is mixed with the diluent inside the diluting container, thus producing a diluted sample. In an aspirating position of the sampling pipette 22, it aspirates a given amount of the diluted sample. In an injecting position of the reaction turntable 5, the aspirated diluted sample is injected into the reaction container 51.

A stirring device 23 and a washing device 24 are disposed around the diluting turntable 2, as well as the diluting pipette 12 and the sampling pipette 22, to stir the diluted sample and to wash the diluting containers. To permit these devices to be arranged with sufficient degrees of freedom, the diluting turntable 21 is advanced incrementally in a manner described later.

The reagent pipettes 32 and 42 take in first and second reagents, respectively, from reagent containers 31 and 41, respectively, and inject them, at injecting positions, into the reaction containers 51 in which the diluted sample has been already introduced. The absorbance of each aliquot of diluted sample mixed with either reagent is kept detected for a given time at a detection position D by a detector 52. The reaction container 51 undergone the detection is washed by the washing device 53 in a washing position W. The various operations, such as the operation of the turntables, the operation of the pipettes, the operation of the stirring device, the operation of the washing device, and the operation of the detector, are under control of a control unit consisting, for example, of a computer (not shown).

In the present invention, the original sample is reacted after diluted in this way. The necessity of the dilution is next described. As described previously, the minimum volume of liquid that the instrument can meter out has a limitation. Where a given amount of liquid is delivered from a pipette, the minimum amount of liquid that can be metered with sufficient reproducibility is about 3 $\mu$l, taking account of the fact that when the discharge ends, the liquid mass breaks in a nonreproducible manner around the tip of the pipette.

In a biochemical analyzer, 300 $\mu$l of reagent and 3 $\mu$l of sample (=100:1) are introduced into each reaction container. This ratio of 100:1 is determined, taking account of the saturation of the detected absorbance and the magnitude of the detected signal. In particular, if the ratio of the sample is too great, the detected absorbance saturates, thus narrowing the dynamic range. If the ratio of the sample is too small, the detected signal is too small, thereby deteriorating the detection accuracy. Taking account of these factors, the above-described ratio is set so that the variations in the absorbance effectively lie within the dynamic range of the detector.

On the other hand, reagents are expensive and so it is desired to minimize the amounts of reagents used. Accordingly, if the operator wants to decrease the reagent introduced into each reaction container down to 100 $\mu$l, the volume of the sample is required to be set to 1 $\mu$l because of the relation with the dynamic range of the detector. However, this amount 1 $\mu$l is below the minimum metered amount. Hence, it is impossible to meter reproducibly and accurately.

If the sample is diluted five times, it follows that 5 $\mu$l of diluted sample contains 1 $\mu$l of the original sample. Therefore, even if the volume of the reagent is reduced down to 100 $\mu$l, the dynamic range of the detector cannot be exceeded. For example, if the operator causes the diluting pipette 12 to draw in 20 $\mu$l of the original sample, dilute it with 80 $\mu$l of a diluent, transfer the diluted sample into the diluting container 21 so that the sample is diluted five times, and causes the sampling pipette to draw in 5 $\mu$l of the diluted sample, then the drawn sample contains 1 $\mu$l of the sample.

The present invention provides the diluting turntable 2, based on the concept described above. On this diluting turntable, the original sample is diluted 4 to 10 times. This produces increased amounts of diluted sample. Relatively large metered amounts of diluted sample are put into the reaction containers. Consequently, the amounts of reagents used can be reduced. At the same time, aliquots of sample can be metered accurately.

Figure 2A:
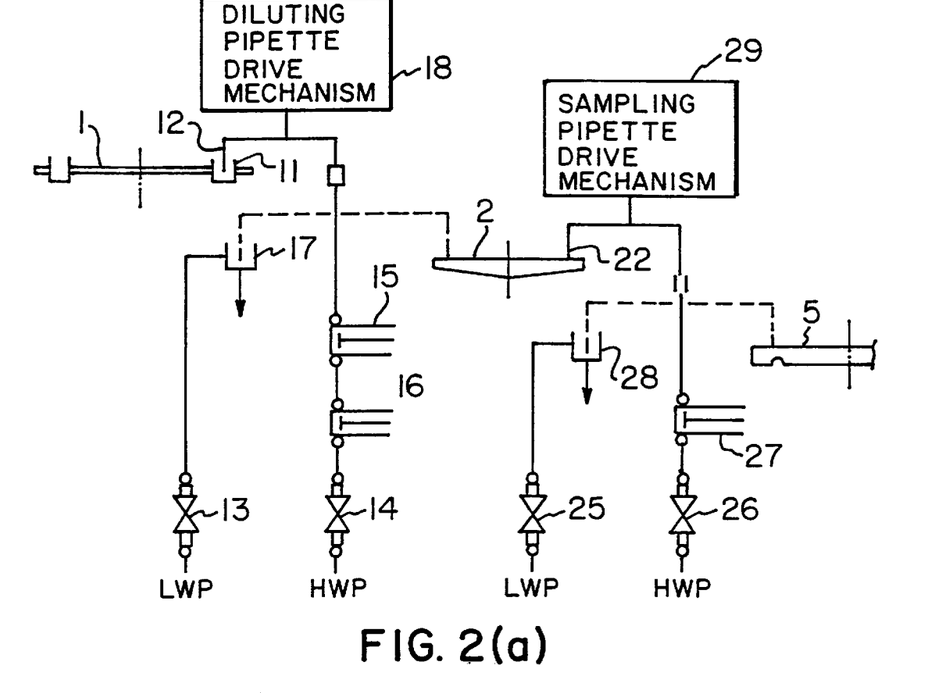
FIGS. 2(a) and 2(b) are views illustrating a diluting system used in the analyzer shown in FIG. 1.
Figure 2B:
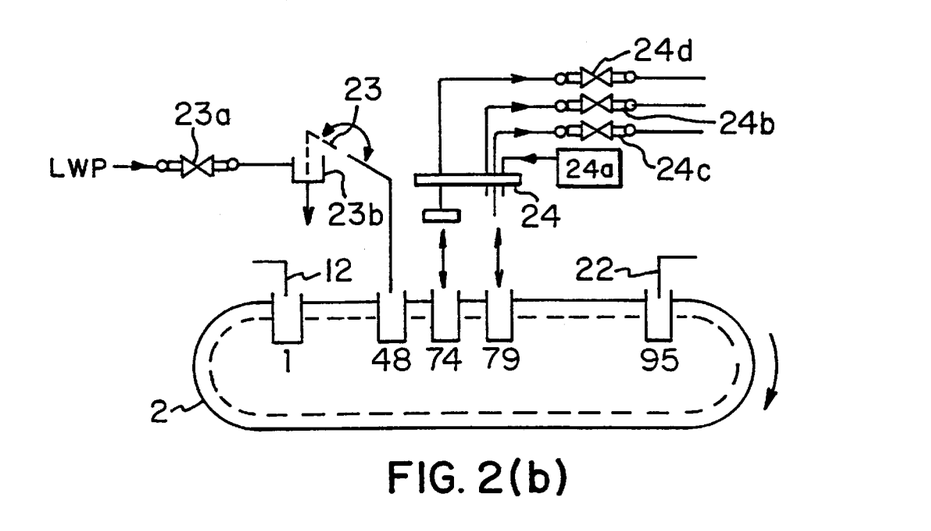

FIGS. 2(a) and 2(b) show a diluting mechanism used in the biochemical analyzer described above. The diluting pipette 12 is rotated between the sample turntable 1 and the diluting turntable 2 and from either turntable into a washing bottle 17 by a diluting pipette drive mechanism 18. This drive mechanism 18 is also equipped with a mechanism to move the pipette 12 up and down so that the height of the pipette 12 is adjusted to any approaching one of the turntables 1, 2 and the washing bottle 17.

It is assumed that the original sample is diluted five times. First, a diluent pump 16 draws in 150 $\mu$l of diluent (normally water) via a valve 14 and holds the drawn diluent. Under this condition, the diluting pipette 12 is filled with the diluent up to its tip. Then, the diluting pipette 12 is inserted into the sample container 11. A sample-aspirating pump 15 is operated to draw 30 $\mu$l, for example, of sample into the front end portion of the diluting pipette 12. Subsequently, the diluting pipette 12 is moved to the diluting container 21, and the diluting pump 16 is operated to discharge the 150 $\mu$l of diluent previously aspirated from the pump. As a result, 30 $\mu$l of sample and 120 $\mu$l of diluent are discharged into the diluting container 21. In consequence, a diluted sample is prepared inside the diluting container by diluting the original sample five times.

On finishing the diluting operation, the diluting pipette 12 is moved into the washing bottle 17, where the pipette is washed. The inside of the diluting pipette 12 is washed with a high-pressure cleaning liquid sent from a high-pressure washing pump HWP via the valve 14. The outside is washed with a cleaning liquid sent from a low-pressure washing pump LWP. The cleaning liquid sent from the high-pressure washing pump HWP is water deaerated so that no bubbles are left in the pipette; otherwise the metering operation would produce errors. This cleaning liquid is also used as a diluent.

To enhance the washing effect, a high pressure is applied to the cleaning liquid from the high-pressure washing pump HWP. As a result, the cleaning liquid is swiftly swept through the diluting pipette to wash away the remaining sample almost fully. Since the low-pressure washing pump LWP acts to wash the outside of the pipette, the pump LWP delivers a low-pressure cleaning liquid. The used cleaning liquids are drained into a waste tank.

The sampling pipette 22 is rotated between the diluting turntable 2 and the reaction turntable 5 and from either turntable into a washing bottle 28 by a sampling pipette drive mechanism 29. This drive mechanism 29 is also equipped with a mechanism to move the pipette 22 up and down so that the height of the pipette 22 is adjusted to any approaching one of the turntables 2, 5 and the washing bottle 28.

When the sampling pipette drive mechanism 29 moves the sampling pipette 22 to one diluting container on the diluting turntable 2, a sampling pump 27 is operated to draw 5 $\mu$l, for example, of diluted sample into the pipette. When the pipette 22 subsequently arrives at one reaction container 51 on the reaction turntable, the sampling pump 27 is operated to discharge the 5 $\mu$l of drawn diluted sample into the reaction container. The result is that the diluted sample containing 1 $\mu$l of the original sample is injected into the reaction container. The used sampling pipette 22 is washed in the washing bottle 28. In the same way as in the case of the diluting pipette, the inside of the sampling pipette 22 is washed with the cleaning liquid sent from the high-pressure washing pump HWP. The outside is washed with the low-pressure cleaning liquid sent from the low-pressure washing pump LWP. The used cleaning liquids are drained off into the waste tank.

FIG. 2(b) illustrates washing, dilution, and stirring performed on the diluting turntable. Let N be the total number of the diluting containers arranged circumferentially on the diluting turntable. These diluting containers are spaced from each other by a uniform pitch. The diluting turntable 1 is rotated incrementally in one direction, M pitches at a time. M and N do not have any common factor.

For example, 120 diluting containers are set on the diluting turntable. This turntable is rotated through an angle corresponding to 47 diluting containers at a time. After coming to a halt for a short time, the turntable 1 is rotated in the same direction through the same angle corresponding to the next 47 diluting containers. Subsequently, these incremental movement and halt are repeated. Suppose that 120 angular positions are assigned to the circumference of the diluting turntable according to the arrangement of the diluting containers. If a diluted original sample is injected into the diluting container in position 1, this container arrives at position 48 and halts there after the next incremental movement. Subsequently, this container arrives at positions 1, 48, 95, . . . , 79, . . . , 74, and 1 sequentially.

At position 48, stirring is done. At position 95, the sampling pipette 22 takes in a required amount of the stirred, diluted sample. At position 79, the remaining diluted sample is drained off and washing is done. At position 74, the washed diluting container is dried.

The stirring device 23 has a stirring rod 23c reciprocated between the diluting container 21 and a washing bottle 23b.

At position 48, the stirring rod 23c stirs the diluted sample in the diluting container. In the washing bottle 23b, the stirring rod 23c is washed with the cleaning liquid sent from the low-pressure washing pump LWP via a solenoid valve 23a.

The wash/dry mechanism 24 washes the diluting container at position 79 and, at the same time, dries the washed diluted container at position 74. In particular, at position 79, the remaining diluted sample is drawn in via a solenoid valve 24c. Then, a washing pump 24a injects a given amount of cleaning liquid into the diluting container. At this time, the cleaning liquid is aspirated from the top of the diluting container under a negative pressure via a solenoid valve 24b to prevent the cleaning liquid from flowing over the diluting container. The injected cleaning liquid is aspirated under a negative pressure via the solenoid valve 24c that is again opened. Subsequently, injection of the cleaning liquid and aspiration are repeated twice, for example, thus finishing the washing operation. At position 74, the cleaning liquid adhering to the inner wall of the diluting container is attracted via a solenoid valve 24d, and the diluting container is dried.

The original sample is analyzed in terms of specified items. The number of the specified items is determined independently for each different sample. Of course, as the number of items specified for one sample is increased, the amount of diluted sample required for analysis increases. Consequently, more diluted sample must be prepared.

Suppose that the sample is diluted five times. In one case, the amount of diluted sample required for analysis is 150 $\mu$l. In the other case, the amount is 600 $\mu$l. These two cases are now discussed. It is assumed that 150 $\mu$l of diluted sample and 600 $\mu$l of diluted sample should be prepared in one diluting operation. For the 150 $\mu$l of diluted sample, it is necessary to send 30 $\mu$l of original sample and 120 $\mu$l of diluent from the diluting pipette into the diluting container. For the 600 $\mu$l, it is necessary to transfer 120 $\mu$l of original sample and 480 $\mu$l of diluent from the diluting pipette into the diluting container.

If the amount of aspirated original sample and the amount of the diluent introduced into the diluting container in one operation vary in this way, the proportionality of the amount of the discharged liquid to the amount of the aspirated liquid does not hold. As a result, the factor by which the sample is diluted changes. More specifically, the inside of the pipette that aspirates and discharges liquid is wetted with liquid and thus the liquid remains on the inner wall surface. For this reason, the movement of the pump that draws in and discharges liquid is not completely coincident with the amount of liquid aspirated or discharged. Furthermore, the drive mechanism of this pump inevitably involves a play and so the proportionality associated with the amount of movement of the pump is not always high. Therefore, the above-described two cases frequently are not equal in dilution factor. In the former case, 30 $\mu$l of sample and 120 $\mu$l of diluent are drawn in, and 480 $\mu$l of liquid is discharged to accomplish a dilution factor of 5. In the latter case, 120 $\mu$l of sample is aspirated and 480 $\mu$l of diluent is discharged, so that a total amount of 600 $\mu$l is obtained.

Accordingly, in the present invention, the amount of sample drawn into the diluting pipette and the amount of diluent delivered from the pipette in one diluting operation are made equal. That is, a constant amount of diluted sample is prepared in one diluting operation. If more diluted sample is necessary, the same diluting operation is repeated. In this way, an amount of diluted sample required for analysis is obtained.

For example, it is assumed that the amount of original sample drawn in and the amount of diluent discharged are maintained at 30 µl and 120 µl, respectively. That is, 150 µl of diluted sample is prepared in one diluting operation. Suppose that the amounts of diluted sample necessary for analysis are 300 µl, 450 µl, and 600 µl, respectively. In this case, 2, 3, and 4 diluting operations are performed, respectively. If these amounts of diluted sample are created in a diluting container that can hold up to 300 µl, then the associated factors are given in the following Table 1.

TABLE 1

|   | amount of original sample | amount of diluent | amount of diluted sample | number of used diluting containers | number of diluting operations |
|---|---|---|---|---|---|
| 1 | 30 µl | 120 µl | 150 µl | 1 | 1 |
| 2 | 30 µl × 2 | 120 µl × 2 | 300 µl | 1 | 2 |
| 3 | 30 µl × 3 | 120 µl × 3 | 450 µl | 2 | 3 |
| 4 | 30 µl × 4 | 120 µl × 4 | 600 µl | 2 | 4 |

The dilution factor of the sample can be maintained constant by regulating the amount of aspirated sample and the amount of discharged diluent in this way. Also, an amount of diluted sample necessary for analysis can be obtained by repeating the suction and delivery of given amounts.

In one conceivable method, one diluting container is disposed for each one sample. Diluted sample necessary for analysis may be all held in the single container. Where all items of analysis are specified, a maximum amount of diluted sample is necessary. At this time, the diluting container must large enough to hold the maximum amount of diluted sample. Such a large diluting container has a large dead volume that is left behind and cannot be aspirated. This increases the amounts of wasted sample and diluent. Also, the number of diluted containers placed on the diluting turntable decreases. If the number is increased, the diluting turntable is increased in size and thus the whole instrument is made larger.

Accordingly, in the present invention, diluting containers each having a small capacity are used. Where a large amount of diluted sample is necessary, plural diluting containers are used for one sample. For example, as shown in Table 1 above, each diluting container has a capacity of 300 µl. The diluted sample can be divided into aliquots up to 300 µl. Where the amount of the required diluted sample is 150 µl or 300 µl, one diluting container is employed. Where the volume of the required diluted sample is 450 µl or 600 µl, two diluting containers are used. Where the amount of the necessitated diluted sample is in excess of 300 µl, the number of diluting containers used is increased accordingly.

As a result, the dead volume of the container can be reduced. More diluting containers can be arranged on a small-sized diluting turntable. Hence, the instrument can be miniaturized.

The diluting containers are conveyed by the diluting turntable in a manner described below. Let N be the total number of the diluting containers arranged circumferentially on the diluting turntable. These diluting containers are spaced from each other by a uniform pitch. The diluting turntable is rotated in M pitches at a time. Notice that M and N do not have any common factor, excluding 1. Thus, all the diluting containers can be successively used. Furthermore, the pipette and the cleaning mechanism can be set at positions that are better than where the containers are rotated in one pitch at a time, from a viewpoint of design of the instrument.

Assuming that N=15 and M=4, the principle of conveyance of the diluting containers in accordance with the invention is next described by referring to FIGS. 3(*a*) and 3(*b*). In FIG. 3(*a*), 15 diluting containers a–o are circumferentially uniformly spaced from each other on the diluting turntable with a given pitch. The turntable is rotated in a clockwise direction incrementally, 4 pitches at a time. Whenever the turntable halts, the sample and the diluent are discharged in the discharging position of the diluting pipette. In the 3 other positions, stirring, aspiration by the sampling pipette, and washing are respectively done. In FIG. 3(*a*), the discharging position of the diluting pipette is indicated by numeral 1. The diluting containers come to a halt at positions 1–15.

Under the condition shown in FIG. 3(*a*), the diluting turntable 2 is rotated in a clockwise direction indicated by the arrow, 4 pitches (M=4) at a time. The diluting containers a, e, i, m, b, f, j, n, c, g, k, o, d, h, and l are successively brought into the discharging position of the diluting pipette. That is, when the turntable is rotated in 15 steps, every diluting container is once brought into the discharging position 1 of the diluting pipette.

FIG. 3(*b*) shows movement of the diluting container a as the turntable is rotated in steps from the position shown in FIG. 3(*a*). At the first halt time, the container a comes to a halt at position 1. At the second halt time, it comes to a halt at position 5. At the third halt time, it comes to a halt at position 9. The same principle applies to the other 14 diluting containers.

Figure 3A:
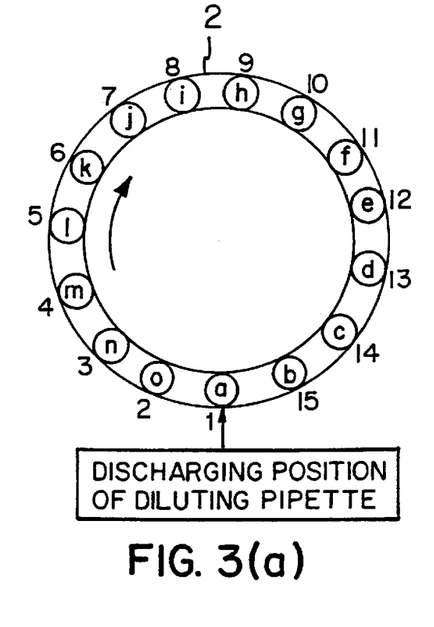
FIGS. 3(a)–3(d) are top plan views illustrating a method of conveying diluting containers through the analyzer shown in FIG. 1.
Figure 3B:
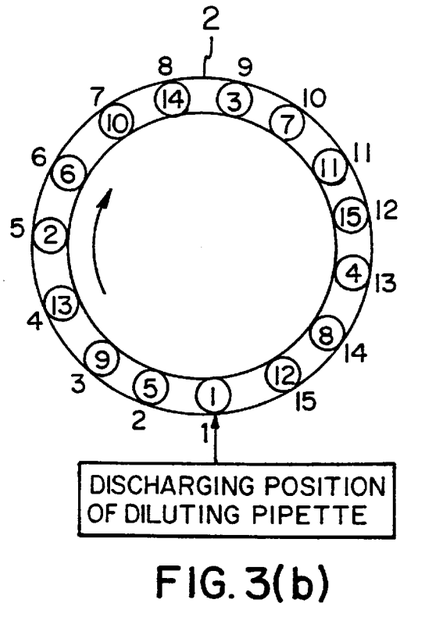
Figure 3C:
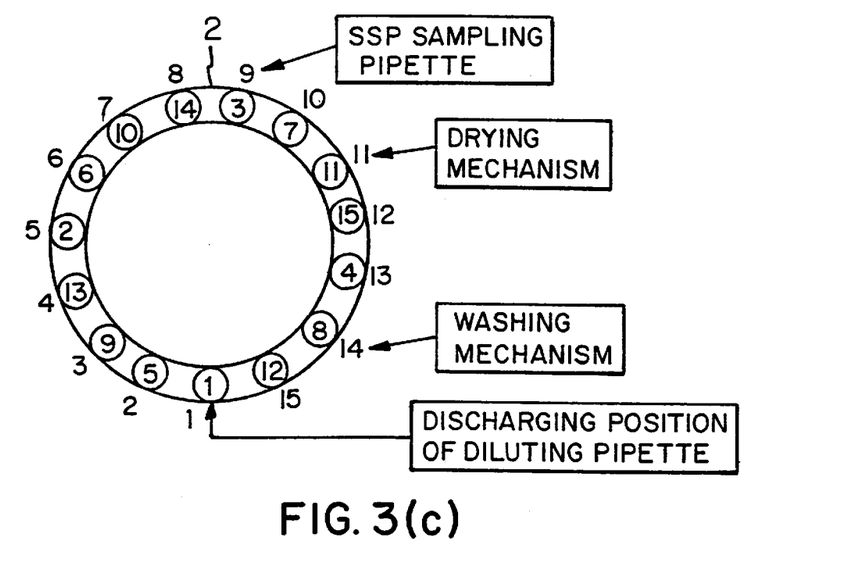
Figure 3D:
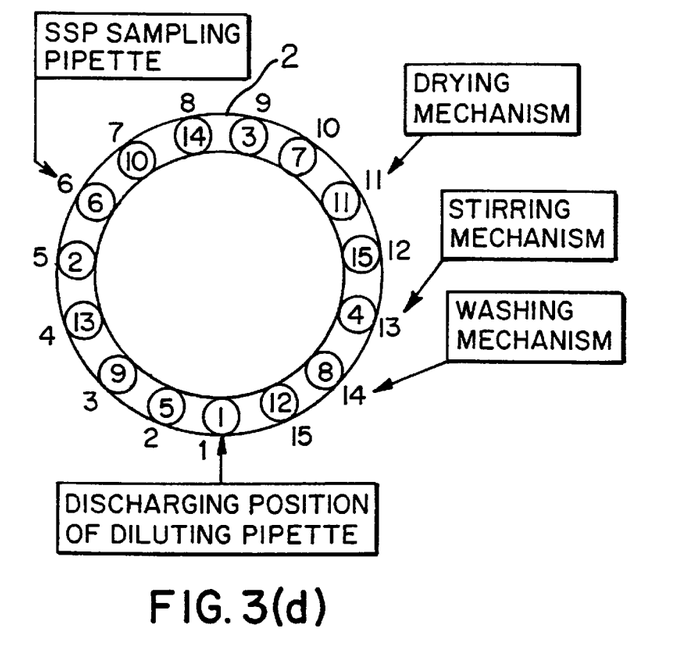

In this way, the diluting containers coming to a halt at the discharging position of the diluting pipette are rotated in steps. Whenever each container is rotated in one step, the container is rotated in 4 pitches. Therefore, the following arrangement can be adopted. As shown in FIG. 3(*c*), a stirring mechanism is disposed at position 5 to perform a stirring operation. The sampling pipette is located at position 9 to effect a sampling operation. A washing mechanism is placed at position 14 to perform a washing operation. A drying mechanism is installed at position 11 to effect a drying operation. In this arrangement, the various mechanisms are not very close to each other and, therefore, any countermeasure for preventing the mechanisms from interfering from each other can be omitted.

As shown in FIG. 3(*d*), it is also possible to place the stirring mechanism, the sampling pipette, the washing mechanism, and the drying mechanism at positions 13, 6, 14, and 11, respectively.

In this way, where the novel method of conveying the diluting containers is used, the various mechanisms (i.e., the diluting pipette, the stirring mechanism, the sampling pipette, the washing mechanism, and the drying mechanism) can be placed with increased degrees of freedom. The construction of the instrument can be easily optimized.

In the example shown in FIGS. 3(*a*)–3(*d*), the number of the containers is set to 15 for simplicity of illustration. The containers can be arranged with greater degrees of freedom by increasing the number. We now give an example. The number of installed diluting containers is 120. The turntable is rotated in 47 pitches at a time. At position 1, the diluting pipette (DPP) injects an original sample and a diluent. The stirring device is represented by MIX. The sampling pipette is represented by SPP. The washing device is represented by W. The drying mechanism is represented by C. The following sequence can be adopted:

1 (DPP), 48(MIX), 95(SPP), 22, 69, 116, 43, 90, 17, 64, 111, 38, 85, 12, 59, 106, 33, 80, 7, 54, 101, 28, 75, 2, 49, 96, 23, 70, 117, 44, 91, 18, 65, 112, 39, 86, 13, 60, 107, 34, 81, 8, 55, 102, 29, 76, 3, 50, 97, 24, 71, 118, 45, 92, 19, 66, 113, 40, 87, 14, 61, 108, 35, 82, 9, 56, 103, 30, 77, 4, 51, 98, 25, 72, 119, 46, 93, 20, 67, 114, 41, 88, 15, 62, 109, 36, 83, 10, 57, 104, 31, 78, 5, 52, 99, 26, 73, 120, 47, 94, 21, 68, 115, 42, 89, 16, 63, 110, 37, 84, 11, 58, 105, 32, 79(W), 6, 53, 100, 27, 74(C), and 1. This sequence is described in detail below.
   (1) At position 1, the diluting pipette (DPP) injects the original sample and the diluent into some diluting container.
   (2) The diluting turntable is rotated in 47 pitches in one step and comes to a halt. As a result, the above-described diluting container is moved into position 48.
   (3) At position 48, the stirring device (MIX) stirs the sample and diluent.
   (4) The diluting turntable is rotated further in 47 pitches in one step and comes to a halt. The container arrives at position 95.
   (5) At position 95, the sampling pipette (SPP) draws in a required amount of the diluted sample from the diluting container.
   (6) The turntable is further rotated in 112 steps, so that the diluting container reaches position 79.
   (7) At position 79, the diluting container is washed by the washing mechanism W.
   (8) The turntable is further rotated in 5 steps. The container arrives at position 74.
   (9) At position 74, the cleaning liquid is cleared from the diluting container by the drying mechanism C and thus the container is dried.

These operations are performed where a diluted sample in one diluting container is analyzed in terms of one item. It may be sometimes necessary to analyze a diluted sample in one diluting container in terms of plural items. Plural different reagents corresponding to the items of analysis are placed on the reagent turntable. In this embodiment, the sample can be analyzed, for example, in terms of up to 40 items. Where one diluted sample is analyzed in terms of plural items, the following operation is carried out.

For illustration, containers holding a diluted sample are used successively, and numbers such as No. 1, No. 2, etc. are given to them.

(1) When the No. 1 diluting container arrives at position 1, the diluting pipette (DPP) injects a first original sample and a diluent.
(2) The diluting turntable is rotated in 47 pitches in 1 step. The No. 1 container is moved into position 48.
(3) At position 48, the stirring device (MIX) stirs the liquids in the No. 1 container. At the same time, the diluting pipette introduces a second original sample and a diluent into the No. 2 diluting container.
(4) The diluting turntable is further rotated in 47 pitches in 1 step. The No. 1 container reaches position 95.
(5) At position 95, the diluting pipette takes in a diluted sample from the No. 1 container for the first item of analysis. At this time, the diluted sample of the second original sample in the No. 2 container is stirred at position 48. A third original sample and a diluent are injected into the No. 3 diluting container at position 1.
(6) At position 95, the sampling pipette (SPP) takes in a diluted sample from the No. 1 container for the second item of analysis. From now on, the sampling of the diluted sample is repeated necessary times at position 95. During this process, the diluting turntable is not rotated, and no operations are performed on the other containers.
(7) The diluting turntable is rotated in 47 pitches in 1 step to move the No. 1 container into position 22, the No. 2 container into position 95, the No. 3 container into position 48, and the No. 4 container into position 1. The liquids in the No. 3 containers are stirred. The diluting pipette (DPP) injects a fourth original sample and a diluent into the No. 4 diluting container.
(8) If plural items of analysis are specified for the diluted sample of the second original sample in the No. 2 diluting container, the sampling pipette repeats sampling necessary times at position 95. During this process, the diluting sample does not turn, and no operations are performed on the other containers.
(9) After this, these operations are repeated. Every diluting container reaching position 79 is washed. Every diluting container arriving at position 74 is dried.

In the analytical process described above, it may be necessary to reexamine samples providing data indicating an abnormality. With the prior art automatic biochemical analyzer, the reexamination has been urged to use the original sample. Usually, the original sample is held in a large-sized blood-gathering tube. An instrument having high throughput (i.e., capable of performing a large amount of processing per unit time) needs a large space to keep in stock the already analyzed original sample for a long time in preparation for reexamination. Also, a complex structure is necessary to return the stocked original sample to the position for reexamination.

In contrast, in the present invention, the diluted sample is held on the diluting turntable without being washed away after the diluted sample is aspirated at position 95 until the turntable is rotated in 112 steps. Where reexamination of any diluting container undergone analysis and already providing analytical data is required, the diluting turntable is temporarily rotated so as to bring the diluting container into position 95. At this position 95, the sampling pipette (SPP) again takes in a diluted sample.

For instance, if it is necessary to reexamine the diluted sample in the diluting container arriving at position 87, the diluting turntable is rotated so that this container moves from position 87 to position 95. When the sampling by the sampling pipette ends, the diluting turntable is rotated to shift the diluting container from position 87 to the next position 14. Subsequently, the turntable is rotated in steps in a normal manner. Where reexamination is not required, the aforementioned operations will be repeated.

In this way, the diluting turntable is rotated in M pitches at a time. Let N be the total number of the diluting containers on the diluting turntable. M and N do not have any common factor, excluding 1. This increases the number of degrees of freedom in arranging the pipetting portion relying on the diluting pipette, the stirring portion, and the sampling portion. Consequently, the instrument can be designed ideally.

Furthermore, the components can be so arranged that as the turntable is rotated in steps, the pipetting relying on the diluting pipette, the stirring, and the sampling are successively carried out. Consequently, immediately after aspiration of a sample, it can be analyzed.

Also, diluting containers permitting automatic reexamination and corresponding to 112 stepwise movements as described above can be secured on the diluting turntable. Therefore, automatic reexamination can be carried out with a small space and a simple mechanism.

In addition, the diluted sample prepared in one diluting container can be analyzed in terms of plural items and so the amount of wasted sample can be reduced to a minimum. Also, the accuracy at which the sample is diluted can be improved compared with the case in which the sample is diluted for each individual item.

Moreover, the diluting turntable is not rotated while plural aliquots of sample are being taken from the diluted sample for plural items of analysis. During this processing, aspiration of the original sample, stirring, washing of the diluting container, and so on can be performed. Therefore, the throughput of the sample-diluting system can be set lower than that of the analysis instrument.

Normally, the original sample is metered in conformity with the capability of the analytical unit to process samples. However, the original sample is put in a large blood-collecting tube and manually processed. Therefore, the maximum rate at which the original sample is metered has a limitation. On the other hand, the analytical unit that are only required to inject aliquots of sample into small reaction containers is relatively easy to provide greater throughput. However, if the throughput of the analytical unit is increased, the metering of the sample cannot follow. In consequence, it is difficult to achieve its maximum capability.

Accordingly, in the present invention, the operating speed of the diluting pipette is made lower than that of the sampling pipette. While the sampling pipette is aspirating the sample, the diluted sample is aspirated, discharged, stirred, and stocked. Consequently, a great drop in the throughput of the analytical portion is prevented.

This is described in further detail by giving an example in which the diluting system can process one sample in three seconds and the analytical portion can take in one aliquot of diluted sample in 1.5 seconds.

It is first assumed that the sample in the single diluting container described above is analyzed in terms of plural items.

(1) At position 95, the sampling pipette aspirates a diluted sample from the No. 1 diluting container for a cycle time of 1.5 seconds for the first item of analysis.

(2) At position 95, the sampling pipette aspirates a diluted sample from the No. 1 diluting container for a cycle time of 1.5 seconds for the second item of analysis.

(3) During the cycles (1) and (2) above, or for 3 seconds, the next diluted sample in the No. 2 container is stirred at position 48.

(4) During the cycles (1) and (2) above, or for 3 seconds, a third original sample is injected into the No. 3 diluting container, together with a diluent, at position 1.

(5) At position 95, the sampling pipette aspirates a diluted sample from the No. 1 diluting container for a cycle time of 1.5 seconds for the third item of analysis.

During these process steps, the turntable does not turn, and no operations are performed on the other containers. Subsequently, the above-described process is repeated until aliquots of diluted sample for all specified items of analysis are taken. The same process is repeated when the diluted, second original sample arrives at position 95.

In this manner, normally, the diluted sample in one diluting container is analyzed in terms of plural items. During this analysis, pipetting and stirring of the subsequent samples are done. Therefore, if a diluting system having a low processing rate is adopted, it is unlikely that the throughput of the analytical unit of higher processing rate is deteriorated greatly.

The diluted sample in the No. 1 diluting container may be required to be analyzed in terms of one item, which is an exceptional example and described next.

(1) At position 95, the sampling pipette aspirates a diluted sample from the No. 1 diluting container for a cycle time of 1.5 seconds for the first item of analysis.

(2) Since the second item of analysis is not specified, no work is done for the next cycle of 1.5 seconds.

(3) During the cycles (1) and (2) above, or for 3 seconds, the diluted second sample in the No. 2 container is stirred at position 48.

(4) During the cycles (1) and (2) above, a third original sample is injected into the No. 3 diluting container, together with a diluent, at position 1.

(5) The diluting turntable is rotated in 47 pitches in one step to move the No. 2 diluting container into position 95.

(6) At position 95, the sampling pipette aspirates a diluted sample from the No. 2 diluting container for a cycle time of 1.5 seconds for the first item of analysis.

(7) At position 95, the sampling pipette aspirates a diluted sample from the No. 2 diluting container for a cycle time of 1.5 seconds for the second item of analysis.

(8) During the cycles (6) and (7) above, or for 3 seconds, the diluted second sample in the No. 3 diluting container is stirred.

(9) During the cycles (6) and (7) above, the next sample is injected into the No. 4 diluting container, together with a diluent, for a cycle time of 3 seconds.

(10) At position 95, the sampling pipette aspirates a diluted sample from the No. 2 diluting container for the third item of analysis.

These operations are subsequently repeated until aliquots of the diluted sample for all the items of analysis are taken. The same processing is repeated when the next original sample diluted arrives at position 95.

Reagent pipettes are now described. The prior art analysis instrument has used reagent pipettes of the same diameter. The reagent pipettes are washed before aspiration of sample. Inevitably, the cleaning liquid is left at the tip of each pipette. This remaining cleaning liquid deteriorates the accuracy at which the aspirated sample is metered.

Also, when a reagent is discharged, it inevitably adheres to the tip of the pipette and remains there. The amount of discharged reagent decreases by an amount equal to the amount of the remaining liquid. To prevent the accuracies of the amounts of reagent aspirated and discharged from deteriorating, it is necessary to minimize the diameter of the reagent pipette at its tip. However, as the throughput of the today's automatic biochemical analyzer improves, the time available to aspirate and discharge a reagent is shortened. If the tip is thinned, the viscous resistance of the reagent makes brief aspiration infeasible.

Normally, therefore, the first and second reagents differ in the amount of usage. For example, the amount of the first reagent is 2 to 4 times as much as the amount of the second reagent. Accordingly, in the present invention, the diameter at the tip of the pipette for the first reagent is made different from the diameter at the tip of the pipette for the second reagent. For example, the diameter of the pipette for the first reagent is made 1.5 to 3 times as large as the diameter of the pipette for the second reagent, since the first reagent is aspirated more.

For example, where the first reagent for aspirating and discharging 50 to 150 $\mu$l and the second reagent pipette for aspirating and discharging 20 to 60 $\mu$l are used as shown in FIG. 4, the first reagent pipette has a diameter of 0.4–0.8 mm, while the second reagent pipette has a diameter of 0.2–0.4 mm. The accuracy of the amount of liquid pipetted can be maximized according to the amount of treated reagent by selecting the inside diameters of the pipettes for the first and second reagents according to the amounts of treated reagents.

As described thus far, the present invention yields the following advantages. Since a diluting turntable used for dilution is provided, the amount of used original sample can be reduced. Also, the amount of reagent used can be diminished. An automatic analyzer can be built, using a small diluting turntable. Furthermore, the instrument can be designed with sufficient degrees of freedom. Each sample can be analyzed in terms of plural items with one diluting container. Automatic reexamination can be easily done, using a diluting mechanism. Even if a diluting system having throughput lower than that of the analytical unit is used, the analytical unit can display its ability to the full.

Figure 4A:
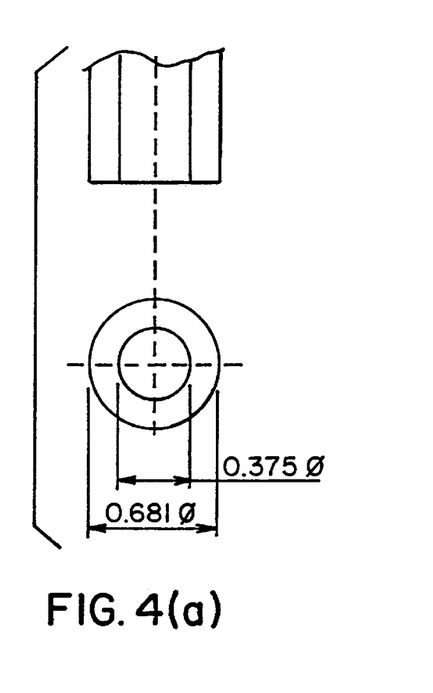
FIG. 4 is a view illustrating reagent pipettes used in the analyzer shown in FIG. 1.
Figure 4B:
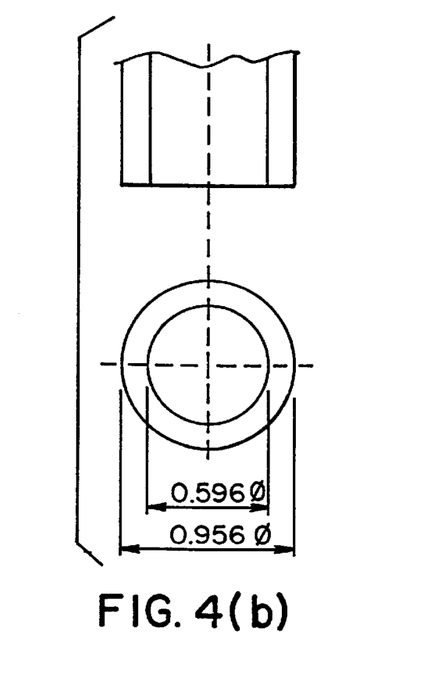

FIG. 4(a) illustrates a second reagent pipette having a capacity of 20 to 60 $\mu$l and FIG. 4(b) illustrates a first reagent pipette having a capacity of 50 to 150 $\mu$l.

Having thus described our invention with the detail and particularity required by the Patent Laws, what is desired protected by Letters Patent is set forth in the following claims.

What is claimed is:

1. An automatic biochemical analyzer comprising:
   a sample turntable having sample containers arranged thereon, said sample containers holding an original sample;
   a diluting turntable having diluting containers arranged thereon;
   a diluting pipette for drawing in said sample from said sample containers and discharging said sample into said diluting containers together with a diluent;
   a reaction container turntable having reaction containers arranged thereon; and
   a sampling pipette for drawing in a diluted sample from said diluting containers and dispensing it into said reaction containers.

2. The automatic biochemical analyzer of claim 1, wherein
   (A) said diluting containers are N in number and substantially equally circumferentially spaced from each other by 1 pitch,
   (B) said diluting turntable is rotated in one direction in M pitches at a time, and
   (C) said M and N do not have any common factor.

3. The automatic biochemical analyzer of claim 1, wherein said diluting containers are 120 in number and substantially equally circumferentially spaced from each other on said diluting turntable by 1 pitch, and wherein said diluting turntable is rotated in one direction in 47 pitches at a time.

4. The automatic biochemical analyzer of claim 2 or 3, wherein said diluting pipette and said sampling pipette are disposed around said diluting turntable, and wherein a stirring mechanism for stirring the diluted sample in said diluting containers, a washing mechanism for washing the inside of the diluting container from which an aliquot of sample has been taken by said sampling pipette, and a drying mechanism for drying the inside of the washed diluting container are mounted around said diluting turntable.

5. The automatic biochemical analyzer of claim 1 or 2, wherein a diluted sample created by one diluting operation by said diluting pipette is maintained at a given volume, and wherein if an amount of diluted sample necessary for analysis exceeds the volume of said diluted sample created by said one diluting operation, said amount of diluted sample necessary for analysis is obtained by plural diluting operations.

6. The automatic biochemical analyzer of claim 1 or 2, wherein said diluting containers arranged on said diluting turntable have the same capacity, and wherein if an amount of diluted sample necessary for analysis exceeds the volume of said diluted sample created by said one diluting operation, said diluting pipette dilutes the same original sample in some or all of said diluting containers.

7. The automatic biochemical analyzer of claim 1 or 2, wherein said sampling pipette takes in aliquots of diluted sample from one diluting container and injects said aliquots into said reaction containers, and wherein said aliquots correspond in number to items of analysis.

8. The automatic biochemical analyzer of claim 1 or 2, wherein if any sample undergone an analysis is required to be reexamined, normal rotation of said diluting turntable is interrupted, said diluting turntable is forced to rotate so that said diluting container holding said sample is brought into a sampling position of said sampling pipette, and said sampling pipette takes in said sample.

9. The automatic biochemical analyzer of claim 1 or 2, wherein said diluting pipette repeats a diluting operation at intervals of a first time and said sampling pipette repeats a sampling operation at intervals of a second time, and wherein said first time is longer than said second time.

* * * * *